United States Patent [19]

Yoshimura et al.

[11] Patent Number: 4,772,125
[45] Date of Patent: Sep. 20, 1988

[54] APPARATUS AND METHOD FOR INSPECTING SOLDERED PORTIONS

[75] Inventors: Kazushi Yoshimura; Takashi Hiroi; Takanori Ninomiya; Toshimitsu Hamada, all of Yokohama; Yasuo Nakagawa, Chigasaki; Kohichi Karasaki, Hadano, all of Japan

[73] Assignee: Hitachi, Ltd., Tokyo, Japan

[21] Appl. No.: 875,974

[22] Filed: Jun. 19, 1986

[30] Foreign Application Priority Data

Jun. 19, 1985 [JP] Japan .................. 60-131744

[51] Int. Cl.$^4$ .................. G01N 21/64; G01N 21/88
[52] U.S. Cl. .................. 356/237; 250/458.1; 358/106
[58] Field of Search .................. 356/237, 240, 387; 250/458.1, 459.1, 461.1; 358/106

[56] References Cited

U.S. PATENT DOCUMENTS

| 3,950,649 | 4/1976 | Yonekubo | 250/458.1 |
| 4,152,723 | 5/1979 | McMahon et al. | 250/458.1 X |
| 4,473,842 | 9/1984 | Suzuki et al. | 358/106 X |
| 4,536,654 | 8/1985 | Vaerman | 250/461.1 X |
| 4,589,140 | 5/1986 | Bishop et al. | 358/106 X |
| 4,641,527 | 2/1987 | Hiroi et al. | 73/582 |

Primary Examiner—Vincent P. McGraw
Attorney, Agent, or Firm—Antonelli, Terry & Wands

[57] ABSTRACT

An apparatus for inspecting an appearance of soldered portions connected between the pads formed on a printed circuit board and leads of an electronic body part. A slit light beam is directed to portions to be inspected and scanned thereon with a light fluorescent image generated from the substrate portion of the printed circuit board and a dark fluorescent image generated from the leads, pads and soldered portions being detected with an image signal being generated in accordance therewith. The image signal is binarized and different functions are extracted from the binarized signal which functions are utilized in connection with other functions and previously obtained data to determine whether an abnormal portion is present or not in a predetermined position on the circuit board.

6 Claims, 10 Drawing Sheets

APPARATUS AND METHOD FOR INSPECTING SOLDERED PORTIONS

BACKGROUND OF THE INVENTION

The present invention relates to an apparatus for inspecting the state of soldered portons of a printed circuit board which carries electronic parts thereon, the measuring apparatus being characterized by the use of an optical means, and also relates to a method for the inspection.

In printed circuit boards used 1n electronic devices such as computers, the mounting of electronic parts thereon tends to become higher in packing density. At the same time, in cosideration of the radiation of heat from electronic parts, there is a tendency toward a narrower spacing between electronic parts and an increased height of parts. The height of parts to the spacing of parts ratio is 4 to 5. Further, leads of parts are becoming shorter with higher integration of electronic parts.

Under such circumstances, at the time of inspecting soldered portions between electronic parts and a printed circuit board, there arises the necessity of looking into a small soldered portion at the bottom between the parts, and such a visual inspection is no longer satisfactory. As to an automatic inspection, it is infeasible according to the prior art because of restrictions imposed on illumination and inspection.

For example, in Japanese Patent Laid-Open Publication No. 171611/83 there is disclosed an automatic inspection using an optical cutting method which recognizes a sectional shape of a soldered portion on a light scanning line to detect a defect. However, since the detection of the sectional shape is performed obliquely, the inconvenience that the portion to be inspected is hidden behind electronic parts arises with increase in packing density of the parts.

On the other hand, as a method of inspecting a soldered portion from just above, there is known a method in which the soldered portion is illuminated uniformly with a conventional vertical irradiation to detect a two-dimensional image. In this case, a strong reflected light is detected locally on part leads or the solder surface, thus resulting in that the image processing at the subsequent pickup system becomes complicated. More particularly, a correct information on shape is not obtainable because of a too broad intensity distribution of reflected light. As means for solving this problem there has been proposed a method, as disclosed in Japanese Patent Laid-Open Publication No. 232344/84, in which an excitation light is applied to a printed circuit board and fluorescence generated from the printed circuit board is detected to detect a defect of a wiring pattern on the same board.

BRIEF SUMMARY OF THE INVENTION

It is the object of the present invention to provide an apparatus capable of inspecting soldered portions between electronic parts mounted at a high packing density and a printed circuit board which carries the electronic parts thereon, as well as a method for the inspection. More particularly, disclosed herein are apparatus and method in which, while a soldered portion is irradiated with a slit beam from the gap between electronic parts, the slit beam is scanned to detect an image concerned with the said scanning and the detected image is subjected to a signal processing.

The present invention is characterized in that a slit beam containing a predetermined excitation light is applied under scanning to a soldered portion of a printed circuit board and at about the same time a silhouette image of the soldered portion with fluorescence generated from the printed circuit board for the background is analyzed to judge whether or not there is a defect such as bridge or dislocation in the soldered portion.

The present invention is further characterized by an optical system which radiates light vertically of a printed circuit board to be inspected thereby making detection and at the same time performs scanning. In such an optical system it is also possible to detect a reflected light.

DETAILED DESCRIPTION

Figure 9:
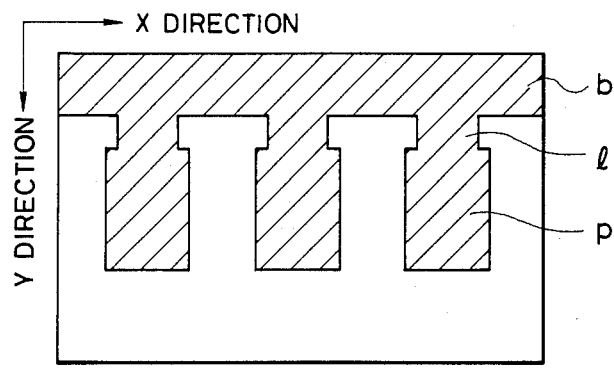
FIG. 9 is a diagram showing an example of an image detected by fluorescence from an object inspected.

FIG. 9 shows an example in which a soldered portion of a flat pack type part permitting a high packing density was picked up from just above and an image obtained by detecting fluorescence emitted from a packaged circuit board was binarized. The hatched area comprises a shady portion b formed by the body of the part, a shady portion l formed by leads of the part, and a shady portion P formed by a pad on the packaged circuit board.

Figure 5:
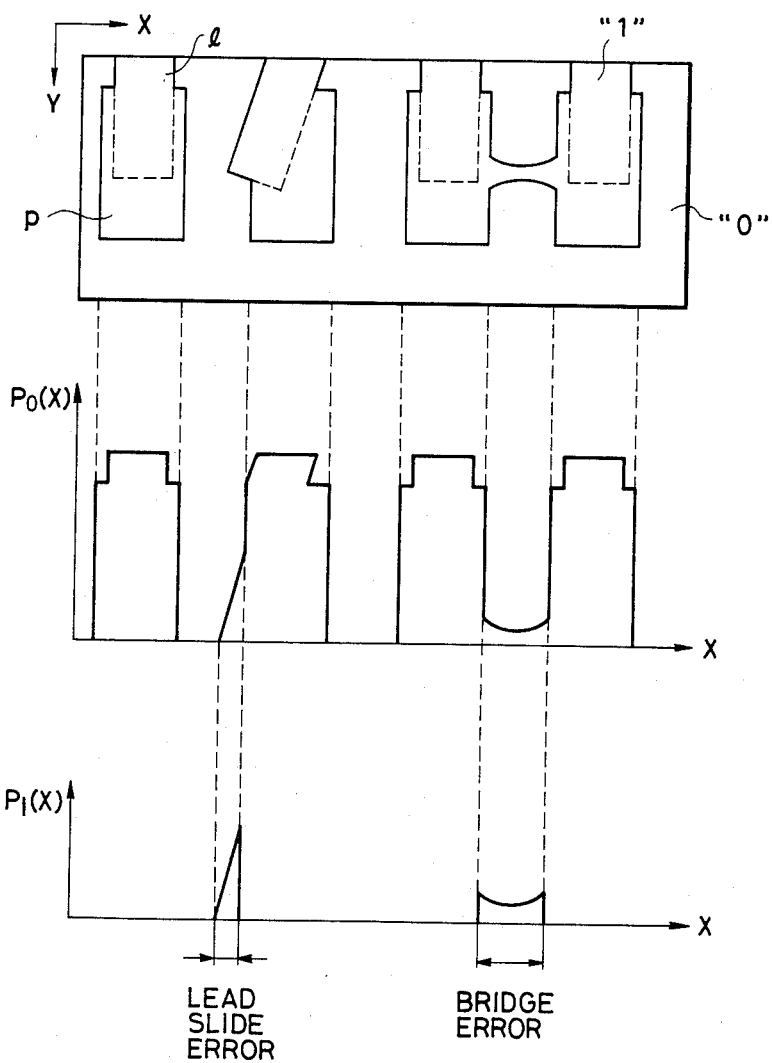
FIG. 5 is a view explanatory of detecting a binarized image according to a projection method.

The above binarized detected image is a combination of picture elements each having a value of 1 or 0 inevitably. In scanning the detected image in a certain direction, by counting the number of picture elements each having a value of "1" for example, it is made possible to convert the image into a one-dimensional data corresponding to a two-dimensional image such as that indicated by a function $P_o(X)$ along the axis of ordinate at the middle portion of FIG. 5. Further, if a processing for obtaining a picture element value of "0" at the pad portion P in FIG. 9, there is obtained a function $P_1(X)$ having the waveform shown at the lower portion of FIG. 5, from which function $P_1(X)$ it is possible to judge whether a defect such as dislocation of bridge or lead is present or not in the soldered portion.

Figure 11A:
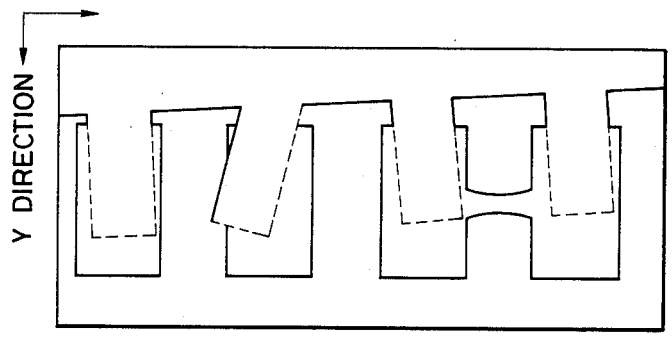
FIG. 11 is a diagram showing an example of an actual fluorescencewise detected image.
Figure 11B:
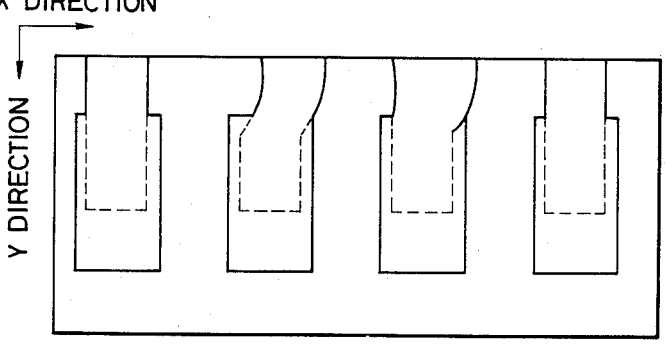

Actually, however, parts are mounted somewhat inclinedly relative to a pad on a printed circuit board, or the leads exposed from parts are inclined or bent, so these states may be judged to be defects of the soldered portion (FIG. 11). It is therefore the object of the present invention to provide a highly reliable inspecting technique free of such erroneous judgment.

[Signal Processing]

Before explanation of an embodiment of the invention, a brief explanation will now be given about the principle of signal processing. It is necesary to change the construction of the function P(X) according to shapes of parts mounted on a printed circuit board.

Figure 6A:
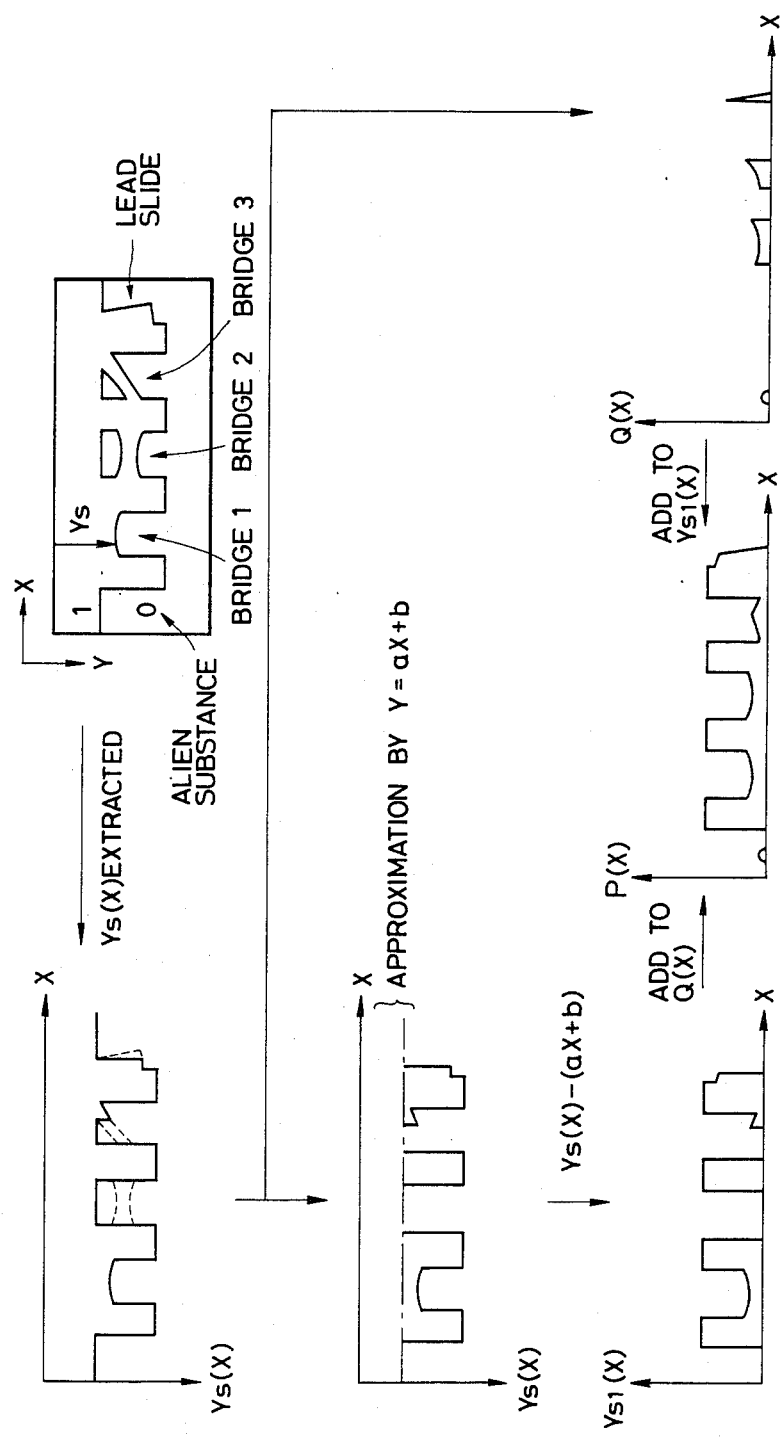
FIG. 6 is an explanatory view of a defect decision in the present invention, in which (a) and (b) correspond to FIGS. 10(a) and 10(b), respectively.
Figure 10A:
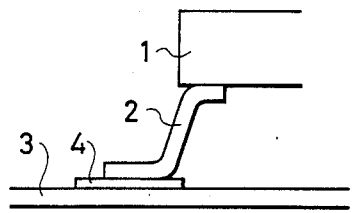
FIG. 10 is a diagram showing a difference in shape between objects inspected.

As to a part of the shape shown in FIG. 10(a), a function of Y coordinates in which the image value changes from "1" to "0" only in Y direction of a detected binary image [right upper portion of FIG. 6(a)], as shown in FIG. 6(a), namely a function Ys(x) of the Y coordinates of a boundary from a dark portion showing the shade of a part or a soldered portion to a light portion showing a substrate portion of a printed circuit board, is determined. The calculation of such boundary will hereinafter be referred to as the calculation of projection data.

Then, a plurality of X coordinates are chosen from between pads (leads) located in predetermined positions, and an approximate line Y=aX+b [left middle portion of FIG. 6(a)] is obtained from the above function Ys(X) [left upper portion of FIG. 6(a)] corresponding to the said X coordinates in order to approximate the straight line of the shade of the part body, further there is obtained a coordinate function $Ys_1(X) = Ys(X)-aX-b$ [left lower portion of FIG. 6(a)] after correction of the influence of the part shade.

Then, with a point on the function Ys(X) as the starting point, a function Q(X) for the calculation of projection data is obtained from a binary image [right upper portion of FIG. 6(a); hereinafter referred to as "binarized image data"]. Further, there is obtained $P(X) = Ys_1(X) + Q(X)$. This P(X) includes all defect data, not including the shade of the part body, and thus it is regarded as defect.

Figure 6B:
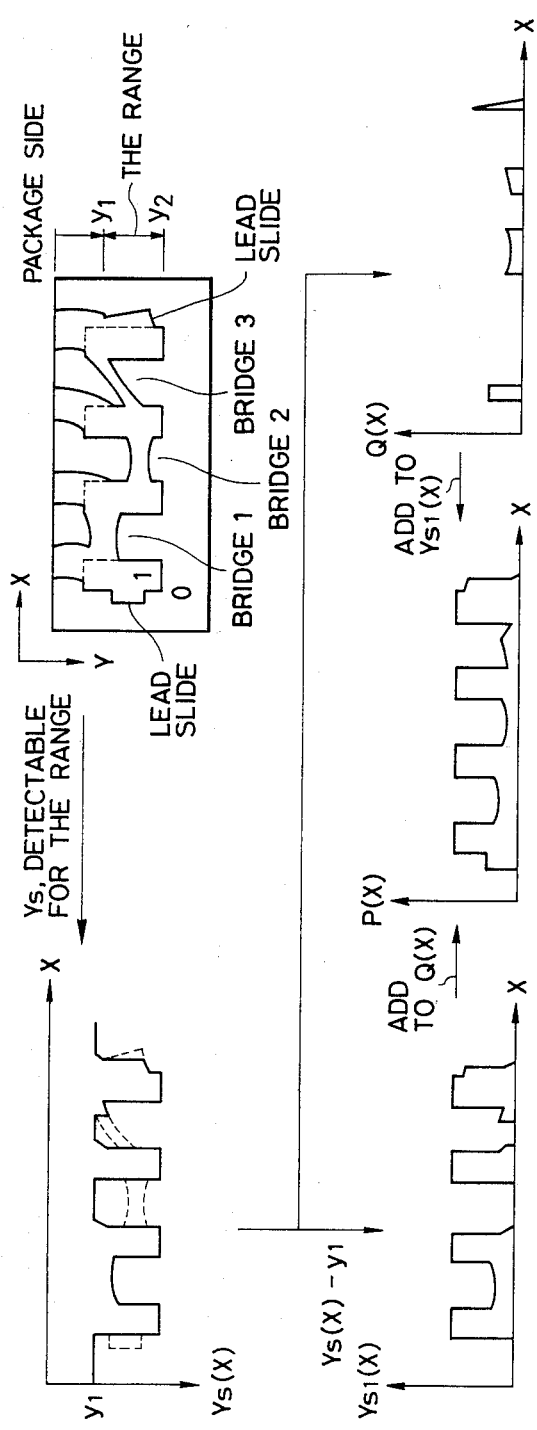
Figure 10B:
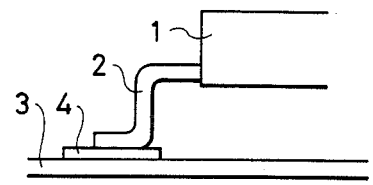

As to a part of the shape shown in FIG. 10(b), there are determined $Ys_1(X)$, Q(X) and P(X) like FIG. 10(a), but the Ys(X) determining range is different. More specifically, only a position direction from a part-side end of pad where a defect is apt to occur, is selected as an inspection range. Therefore, as to Ys(X), only a positive direction of Y axis from $y_1$ is detected as shown in FIG. 6(b).

Since the shade of the part body does not enter the detection field, an approximated part line aX+b becomes equal to $y_1$. As to the other points, like (a), P(X) does not include inclination or bend of part leads and includes all defect data.

[Embodiment]

Figure 1:
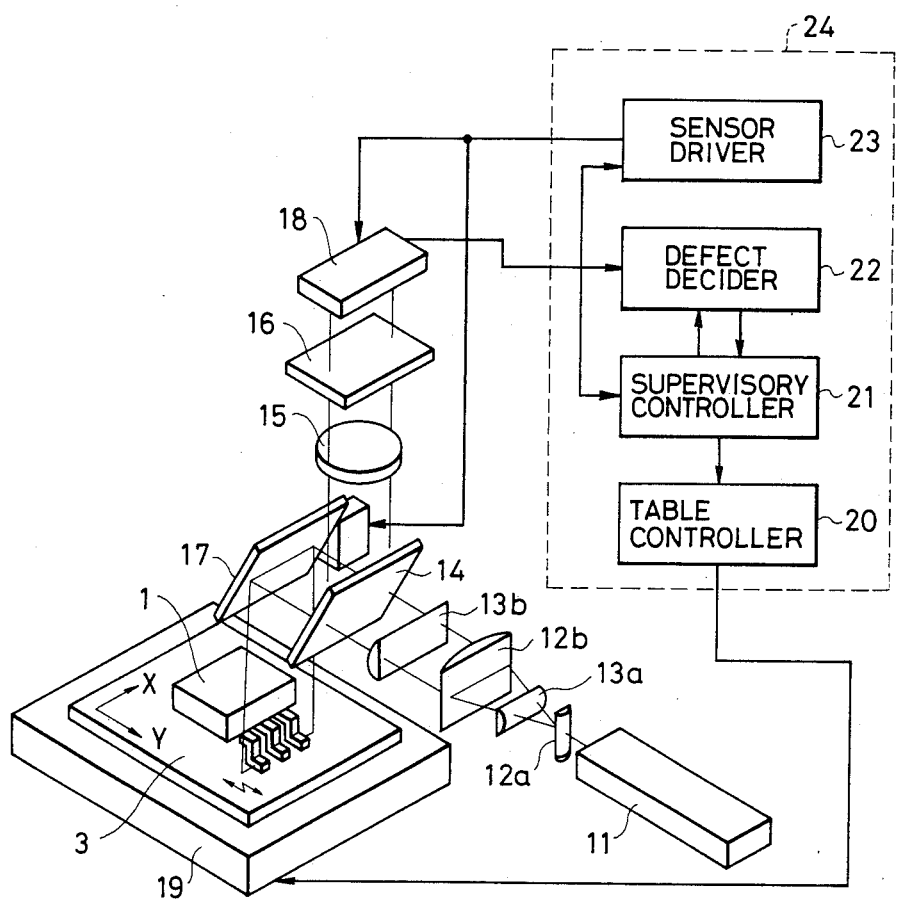
FIG. 1 is an entire construction diagram of an embodiment of the present invention.

(1) FIG. 1 is an entire construction diagram of a soldered portion inspecting apparatus according to an embodiment of the present invention. The inspecting apparatus includes:

an excitation means comprising an Ar laser 11 of a wavelength (λ) of 514 or 488 nm, cylindrical lenses 12a and 12b for expanding a laser beam in X direction, cylindrical lenses 13a and 13b for contracting the laser beam in Y direction, a dichroic mirror 14 for reflecting only excitation light and transmitting fluorescence, and a galvanomirror 17 for scanning an object to be inspected;

a detecting means comprising an optical system 15 for imaging the excited fluorescence, a filter 16 for separating only a fluorescence component contained in a detected light, a galvanomirror 17 for scanning the object being inspected, and a linear sensor 18 for detecting the fluorescence;

an XY table 19 for positioning the object to be inspected; and a control means 24 comprising a sensor driver 23, a table controller 20 for controlling the XY table, a defect decider 22, and a supervisory controller 21.

As to the excitation means, in place of the Ar laser 11 and cylindrical lenses 12, 13 there may be used an ultra high pressure mercury vapor lamp, a focusing lens for focusing the excitation light onto the object being inspected, and a filter for passing only the excitation light therethrough. And as to the detecting means, a TV camera for detecting a fluorescent image may be employed in place of the galvanomirror 17 and the linear sensor 18. Further, in place of scanning over the object by means of the galvanomirror 17, the scanning may be effected by moving the XY table 19.

(2) An outline of the entire inspecting operation will be explained below.

First, a command issues from the supervisory controller 21 to move the XY table 19 to an inspection start position and preparations are made for applying a laser beam to a soldered portion of the object to be inspected.

Then, the XY table 19 is driven to move a lead portion of one side of a flat package 1 to be inspected to an inspecting position so that a slit laser beam is applied to the lead portion of the one side.

In this state the galvanomirror 17 is driven and only a fluorescent component from the substrate portion is detected by the linear sensor 18, followed by pickup of a fluorescent image. This image information is analyzed to judge whether it is a defect or not.

The above operations are repeated in different inspecting positions.

(3) The following description is now provided about the decision of defect.

Figure 2:
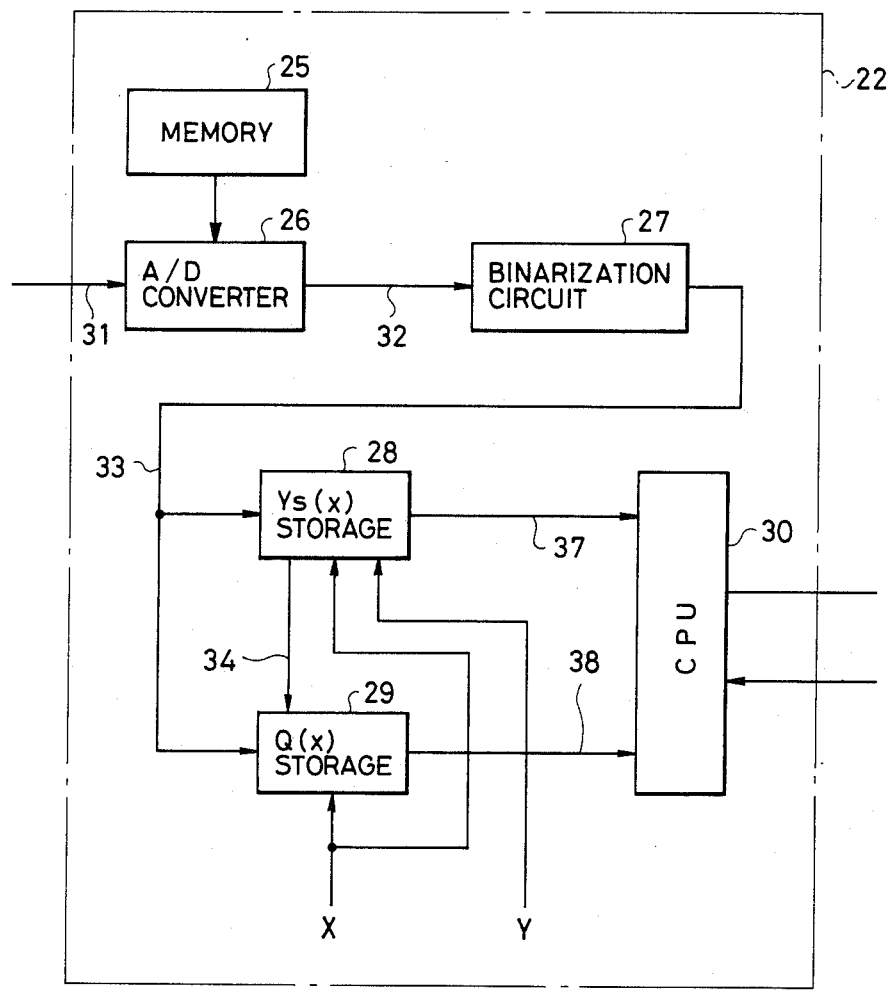
FIG. 2 is a detailed explanatory view of a defect decider 22 used in the apparatus of FIG. 1.

FIG. 2 is a block diagram of the defect decider. It is here assumed that the scanning direction of the linear sensor 18 and that of the galvanomirror 17 are X and Y, respectively. A fluorescent image detected signal 31 obtained by the linear sensor 18 is subjected to shading correction and conversion to digital value by an A/D converter 26 and a shading correction data memory 25.

The shading correction is performed when the light sources is not always in a state of uniform illumination. Laser beam is applied in advance to the substrate portion free of wiring pattern and the fluorescent image concerned is taken in. Further, amounts of correction at various points of image are stored in the shading correction data memory 25 and used for correcting the brightness of image at the time of detection of fluorescence during inspection. For the shading correction, there may be used, for example, the apparatus disclosed in Japanese Patent Laid-Open Publication No. 153328/83.

A fluorescent image detected signal 32 after conversion to a digital value is converted to a binarized image data 33 by means of a binarization circuit 27, which data 33 is fed to a Ys(X) detecting circuit 28 and a Q(X) detecting circuit 29. In the Ys(X) detecting circuit 28, Ys(X) is obtained and a Ys(X) flag 34 is provided to the Q(X) detecting circuit 29 when the corresponding X coordinates are x during the calculation of Ys(X).

The Q(X) detecting circuit 29 determines Q(X) by counting the number of picture element value "1" of the soldered portion and pad portion in the binarized image data 33 which correspond to the X coordinates "x" at the time of output of the Ys(X) flag 34.

At the time when the detection of fluorescent images over one picture plane is completed in the above manner, Ys(X) and Q(X) are stored in the respective detection circuits 28 and 29. These two kinds of data are transferred to a microcomputer 30 (FIG. 2) and processed therein to thereby effect the decision of a defect.

The Ys(X) detecting circuit 28 and the Q(X) detecting circuit 29 will be explained below.

Figure 3:
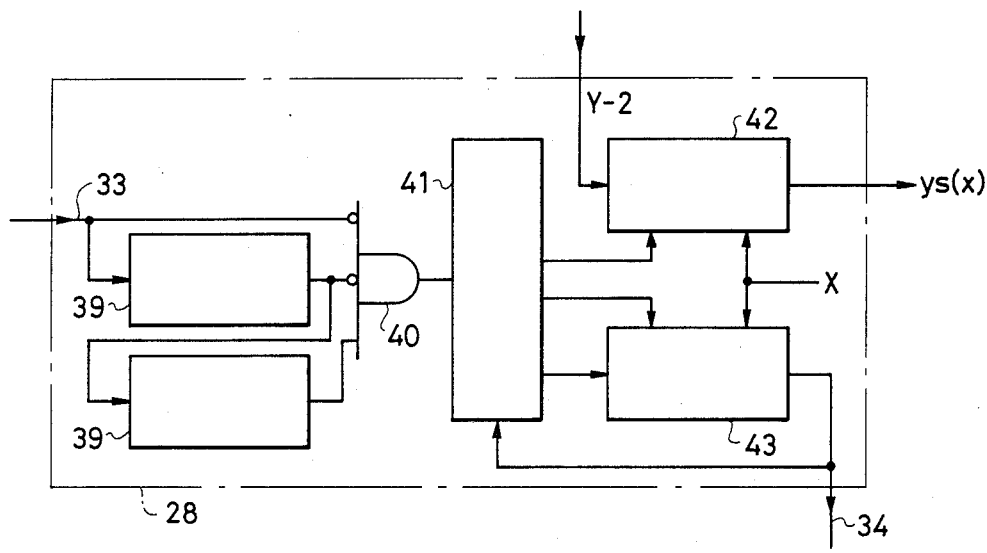
FIG. 3 is a detailed explanatory view of a Ys(X) detecting circuit 28 used in the apparatus of FIG. 2.

FIG. 3 shows an example of construction of the Ys(X) detecting circuit 28, in which, in order to prevent the influence of noise, etc., the portion where the picture element value changes for the first time from "1", i.e. dark portion (shade of the part body or a soldered portion), to "0", i.e. light portion (substrate portion), and where the next Y coordinates are also "0", is assumed to be Ys(X). In this circuit configuration example, a take-out circuit constituted by a shift register 39, and an AND circuit 40, are for detecting a point at which the picture element value, one of conditions of Ys(X), changes from "1" to "0". A Ys(X) memory 42 stores a value of Ys(X) corresponding to X coordinates, while in a Ys(X) flag memory 43 there is stored a flag showing whether the Ys(X) of the X coordinates has already been detected or not. A Ys(X) memory controller 41 controls these memories.

(4) The operation of this circuit will now be explained. In the binarized image data 33 received in this circuit, its coordinates are one of conditions of Ys(X). In the case of a changing point from "1" to "0" and in the case of an initially detected one, the Y coordinates y-2 at that time are written in the Ys(X) memory 42 and a flag indicating that the Ys(X) of the X coordinates has already been detected is set at the Ys(X) flag memory 43.

Figure 4:
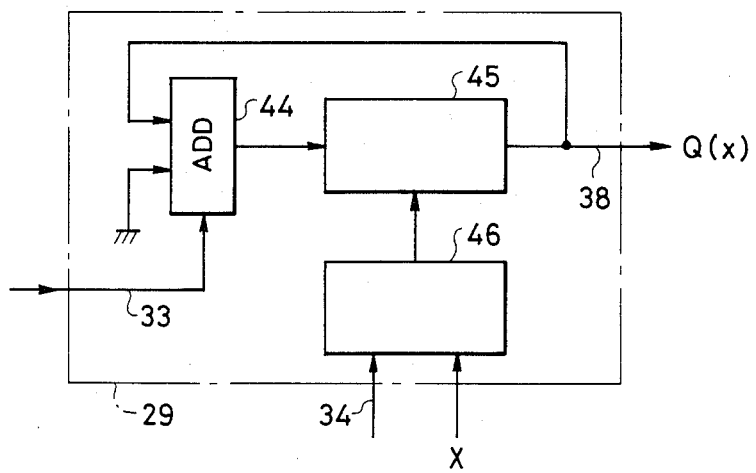
FIG. 4 is a detailed explanatory view of a Q(X) detecting circuit 29 used in the apparatus of FIG. 2.

FIG. 4 shows an example of construction of the Q(X) detecting circuit 29. A Q(X) memory 45 stores the value of Q(X), and an adder 44 constitutes a counter conjointly with the Q(X) memory 45. A Q(X) memory controller 46 controls these devices. The operation of this circuit will now be explained. Where the binarized image data received in this circuit is "1" and it is indicated by the Ys(X) flag 34 that the Ys(X) of the X coordinates "x" concerned has already been detected, the value of the Q(X) memory 45 of the X coordinates is incremented.

In this way there are determined Ys(X) 37 and Q(X) 38. In this embodiment, the $Ys_1(X)$ and P(X) shown in FIGS. 6(a) and 6(b) are subjected to a software processing in the microcomputer 30.

(5) The following is an outline of how the thus-obtained $Ys_1(X)$, P(X) and Q(X) are subjected to a defect decision using a software processing in the microcomputer 30.

Figure 7A:
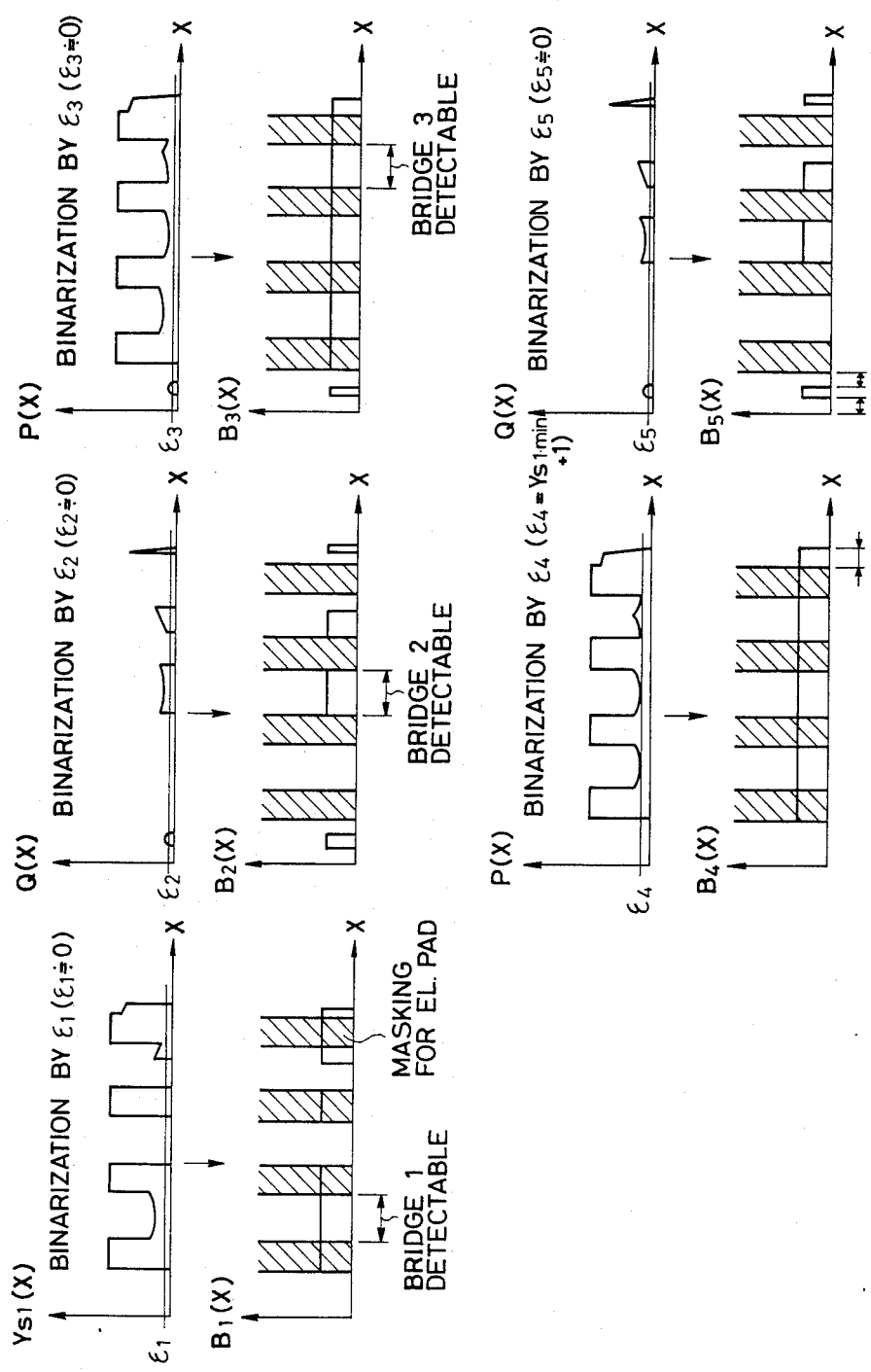
FIG. 7 is an explanatory view of a defect discriminating method according to the present invention, in which (a) and (b) correspond to FIGS. 10(a) and 10(b), respectively.

First, how to detect a bridge in the case of the part shape of FIG. 10(a) shown in FIG. 6(a) will be described. In FIGS. 7(a) and (b), hatched portions indicate leads of parts added for the aid of understanding. As shown in FIG. 7(a), the $Ys_1(X)$, Q(X) and P(X) are binarized with appropriately set values $\epsilon_1$, $\epsilon_2$ and $\epsilon_3$, whereby there are obtained functions $B_1(X)$, $B_2(X)$ and $B_3(X)$. The function B(X) is a fully waveform-shaped function, so by comparing it with a positional information given from design values such as those of leads of a part or a pad on a printed circuit board, there can be detected a bridge. The left lower portion of FIG. 7(a) shows a mode using as $\epsilon_4$ a value obtained by adding 1 to a minimum value of $Ys_1(X)$. In order to detect an alien substance other than bridge, there is set another value $\epsilon_5$, which is shown in the right lower portion of FIG. 7(a).

Figure 7B:
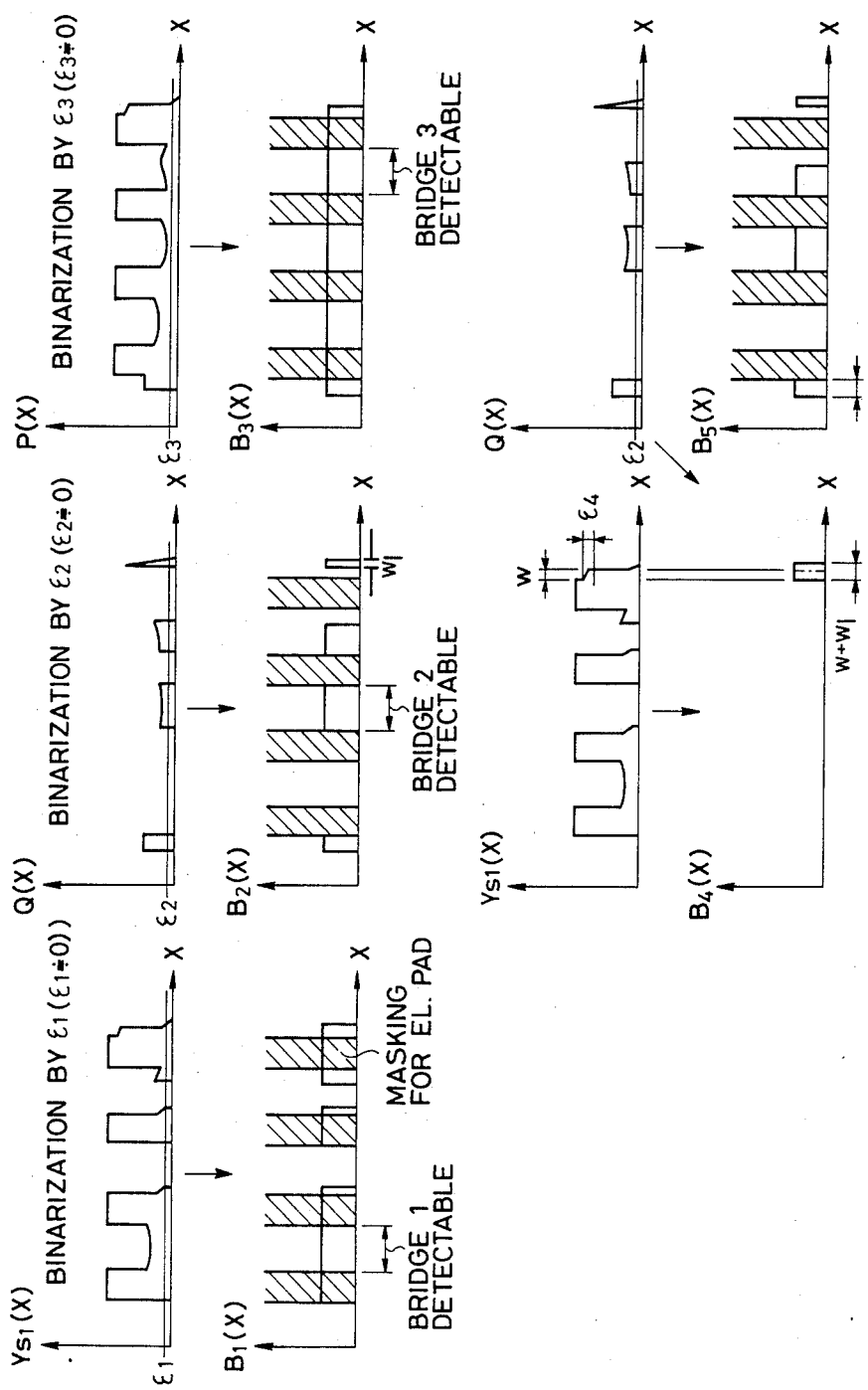
Figure 8:
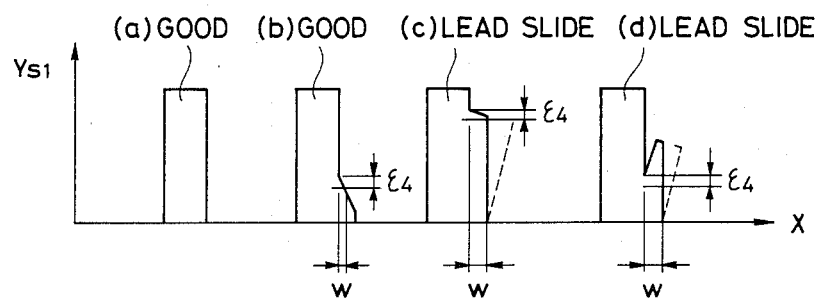
FIG. 8 is a diagram showing a relation between 4 and W at $Y_{si}(X)$ in FIG. 7(b)

On the other hand, in the case of the part shape of FIG. 10(b) shown in FIG. 6(b), the bridge detection is performed in the same way as shown in FIG. 7(b), but in the detection of a lead slide, there is a fear that the bend of the lead shoulder portion will be judged to be a lead slide erroneously. The mode shown at the left lower portion of FIG. 7(b) will be explained below using FIG. 8.

(6) A width W (FIG. 8) obtained by subtracting $\epsilon_4$ from $Ys_1(X)$ which corresponds to X coordinates at right and left ends of the pad will now be considered. At shoulder portions (a) and (b) to be allowed, the W is small. On the other hand, a large W is observed in lead slide. This is utilized as follows. Where W is above a certain value $\epsilon$, it is assumed that the possibility of occurrence of lead slide is high, then a binarized value of Q(X) is added and whether the amount of the slide is larger than a predetermined value or not is judged [left lower portion of FIG. 7(b)].

In the above manner it is possible to effect the decision of a defect without being influenced by the shade of the part body or the lead shoulder portion.

According to this embodiment, the Ys(X) and Q(X) detecting processing which handles two-dimensional data is performed hardwarewise, so it is possible to effect a high-speed defect discriminating processing.

According to another embodiment, all of the Ys(X) detecting circuit 28 and the Q(X) detecting circuit 29 are replaced by the software processing using the microcomputer 30, whereby the apparatus construction can be simplified because it is not necessary to provide a special processing circuit.

According to the present invention, it is possible to attain a highly reliable inspection for soldered portions because the influence of the shape and dimensional tolerances of parts and part leads can be removed.

We claim:

1. An apparatus for inspecting an appearance of a plurality of soldered portions connected between pads formed on a printed circuit board and leads of an electronic body part comprising:

irradiating means for irradiating a slit-like X-direciton excitation light onto leads of an electronic body part extending in a Y-direcition and for scanning in the Y-direction for generating fluorescence from a substrate portion of a printed circuit board on a part of the printed circuit board adjacent a plurality of soldered portions connected between pads formed on the printed circuit board and the leads of the electronic body part;

detecting means for detecting a two-dimensional fluorescent image formed by a light fluorescent image generated from the substance portion of the printed circuit board and a dark fluorescent image generated from said leads, said pads, and said soldered portions, said detecting means including an image detector means for converting said two-dimensional fluorescent image to an image signal;

binarization circuit means for converting said image signal to a binarized signal corresponding to said light fluorescent image and said dark fluorescent image;

Ys(x) detecting means for extracting from said binarized signal a function Ys(x) of Y coordinates for x coordinates of the X-direction indicative of the boundary initially detected as said light fluorescent image from an edge line of a body part proximate to a side edge of said pads in the Y-direction, said Ys(x) detecting means including memory means for storing said function Ys(x);

Q(x) detecting means for extracting a function Q(x) of projection data by adding picture elements corresponding to said dark fluorescent image of said binarized signal detected on an opposite side of said body part for said boundary Ys(x) in the Y-direction for x coordinates of the X-direction, said Q(x) detecting means including memory means for storing said function Q(x);

$Ys_1(x)$ calculating means for calculating a function $Ys_1(x)$ by removing line coordinates previously determined from said function Ys(x) read out from said memory means of the Ys(x) detecting means without being influenced by a shade effect of said body part or a lead shoulder portion; and defect detecting means for detecting at least one defect of a bridge of solder and a lead slide error in accordance with signals $B_1(x)$ and $B_2(x)$ obtained by comparing said function $Ys_1(x)$ obtained by said $Ys_1(x)$ calculating means and said function Q(x) read out from said memory means of the Q(x) detecting means with pad position information B(x). and masking an x-area of said function $Ys_1(x)$ and said function Q(x) by the pad positional information B(x).

2. An apparatus according to claim 1, wherein the pad positional information B(x) of the defect detecting means is predetermined data.

3. An apparatus according to claim 1, wherein said defect detecting means includes adding means for adding said function $Ys_1(x)$ and said function Q(x) to obtain a function P(x), said defect detecting means detecting the defect in accordance with the signal $B_3(x)$ by comparing said function P(x) with the pad positional information B(x), and masking the x-area of said function P(x) by the pad positional information B(x).

4. An apparatus according to claim 1, wherein said defect detecting means detects the defect by utilizing predetermined values $\xi_1$ and $\xi_2$ or $\xi_5$ for each of the function $Ys_1(x)$ and function Q(x).

5. An apparatus according to claim 3, wherein said defect detecting means detects the defect by utilizing predetermined values $\xi_3$ for the function P(x).

6. An apparatus according to claim 1, wherein said defect detecting means further detects as the defect of a lead slide error when a width W which extends outwardly from an end of the pad in the X-direction on a tip of said lead is greater than a predetermined value $\xi_4$.

* * * * *